(12) United States Patent
Racz et al.

(10) Patent No.: US 6,371,943 B1
(45) Date of Patent: Apr. 16, 2002

(54) SPRING TIP NEEDLE COMBINATION

(75) Inventors: Gabor J. Racz, Lubbock, TX (US); Bruce B. Whitcavitch, St. Johnsville, NY (US)

(73) Assignee: Epimed International, Inc., Gloversville, NY (US)

( * ) Notice: Subject to any disclaimer, the term of this patent is extended or adjusted under 35 U.S.C. 154(b) by 0 days.

(21) Appl. No.: 09/353,159

(22) Filed: Jul. 14, 1999

Related U.S. Application Data

(62) Division of application No. 08/925,523, filed on Sep. 8, 1997, now abandoned.

(51) Int. Cl.⁷ .................................................. A61M 5/32
(52) U.S. Cl. ........................ 604/274; 604/272; 604/264
(58) Field of Search .............................. 604/272, 274, 604/523, 264, 273, 524, 525, 528, 164.01, 164.13; 600/585, 462, 433, 434, 435; 606/44; 607/125

(56) References Cited

U.S. PATENT DOCUMENTS

| | | | |
|---|---|---|---|
| 3,682,162 A | * 8/1972 | Colyer | 128/2.1 R |
| 4,405,314 A | 9/1983 | Cope | |
| 4,411,657 A | * 10/1983 | Galindo | 604/274 |
| 4,771,778 A | 9/1988 | Mar | |
| 4,773,432 A | 9/1988 | Rydell | |
| 4,943,278 A | 7/1990 | Euteneuer et al. | |
| 4,971,490 A | 11/1990 | Hawkins | |
| 5,002,559 A | 3/1991 | Tower | |
| 5,156,595 A | 10/1992 | Adams | |
| 5,178,158 A | 1/1993 | De Toledo | |
| 5,226,427 A | 7/1993 | Buckberg et al. | |
| 5,250,059 A | 10/1993 | Andreas et al. | |
| 5,306,236 A | * 4/1994 | Blumenfeld et al. | 604/21 |
| 5,318,041 A | * 6/1994 | DuBois et al. | 607/119 |
| 5,318,525 A | 6/1994 | West et al. | |
| 5,338,300 A | 8/1994 | Cox | |
| 5,385,562 A | 1/1995 | Adams et al. | |
| 5,395,332 A | 3/1995 | Ressemann et al. | |
| 5,405,376 A | * 4/1995 | Mulier et al. | 607/127 |
| 5,415,633 A | * 5/1995 | Lazarus et al. | 604/95 |
| 5,417,658 A | 5/1995 | Loney et al. | |
| 5,423,771 A | * 6/1995 | Imran | 604/281 |
| 5,441,484 A | 8/1995 | Atkinson et al. | |
| 5,449,369 A | * 9/1995 | Imran | 606/159 |
| 5,476,501 A | * 12/1995 | Stewart et al. | 607/127 |
| 5,484,409 A | 1/1996 | Atkinson et al. | |
| 5,500,012 A | * 3/1996 | Brucker et al. | 607/122 |
| 5,522,875 A | * 6/1996 | Gates et al. | 607/127 |
| 5,545,133 A | 8/1996 | Burns et al. | |

(List continued on next page.)

Primary Examiner—Richard K. Seidel
Assistant Examiner—Cris Rodriguez
(74) Attorney, Agent, or Firm—TraskBritt

(57) ABSTRACT

An improved needle for directional placement of the needle into or to a target area, such as a blood vessel or organ, for the purpose of performing an invasive procedure with a minimal amount of trauma to the target area. The needle comprises a connection hub, a needle shaft, and a flexible tip member connected to a distal end of the needle shaft to facilitate maneuvering the needle through tortuous passages within the body. The flexible tip member includes a blunt end that prevents or reduces trauma to tissues and vessels that are contacted with the distal portion of the needle during positioning of the needle. The invention further comprises a flexible-tipped needle having a balloon sealingly attached to a distal end of the spring tip member. The flexible-tipped balloon needle includes an inflatable balloon sealingly connected to the distal end of the flexible tip member. An alternate embodiment comprises a flexible-tipped needle having a balloon sealingly connected, via apertures in the needle shaft, to the bore within the needle shaft of the spring tip member. The invention also includes a flexible-tipped needle having an insulated needle shaft, an insulated flexible-tip member, a blunt conductive end and a conductive wire extending from said blunt conductive end to an apparatus for sending or receiving electromagnetic signals.

4 Claims, 4 Drawing Sheets

U.S. PATENT DOCUMENTS

| | | |
|---|---|---|
| 5,549,580 A | 8/1996 | Diaz |
| 5,567,203 A | 10/1996 | Euteneuer et al. |
| 5,571,087 A | 11/1996 | Ressemann et al. |
| 5,573,522 A | 11/1996 | Houser et al. |
| 5,628,316 A | 5/1997 | Swartz et al. |
| 5,643,197 A * | 7/1997 | Brucker et al. ............... 604/20 |
| 5,882,333 A * | 3/1999 | Schaer et al. ................. 604/95 |
| 6,004,279 A * | 12/1999 | Crowley et al. ............ 600/585 |

* cited by examiner

SPRING TIP NEEDLE COMBINATION

CROSS REFERENCE TO RELATED APPLICATION

This application is a divisional of application Ser. No. 08/925,523, filed Sep. 8, 1997, now abandoned.

BACKGROUND OF THE INVENTION

1. Field of the Invention

The present invention relates to an improved needle for directional and atraumatic placement of the needle into a vascular system or body tissue for the purpose of performing multiple invasive procedures.

2. State of the Art

Needles and needle systems are used extensively in a wide variety of procedures which are performed in various fields of medicine, such as cardiology, radiology, urology, interventional pain management, and internal medicine. The use of needles and needle systems in invasive procedures in various medical fields has become routine due, in part, to the ability of needles to pass through most tissues without causing significant destruction to the tissues.

Conventional hypodermic needles, such as those used with hypodermic syringes in the administration of intravenous fluids, are well known in the medical arts. Hypodermic needles such as these are usually used in conjunction with various types of disposable hypodermic syringes for administration of medications like antibiotics, narcotics, biologicals, and vitamins. Hypodermic needles are also utilized in a number of diagnostic and therapeutic procedures, such as aspiration, blood draws, and biopsies. As more fully described in conjunction with FIG. 1 below, hypodermic needles are typically made of metal, consist of a hub that locks to a tip of the hypodermic syringe by friction or through a locking mechanism (known as Luer-Lock™), and typically include a point (usually in the form of a beveled cutting edge) of varying diameter and length.

Another widely-used type of needle system includes a system that employs a catheter and guide member. Such needle systems generally include a small guide member (e.g., guide wire) which is used to guide a larger hollow catheter to a target area (e.g., a vessel, body cavity, tissue, or organ) within a human or animal body. In use, the guide member is directed to the proximity of the target area using a hollow cannula or needle. The cannula is inserted into the body and positioned with its distal end in contact with or adjacent to the target area within the body. The guide member is advanced through the cannula to the target area. The cannula is then removed and the catheter is advanced over the guide member and into or to the target area. The guide members of these intravascular catheterization systems typically consist of a rigid wire or rod and a flexible tip that enables the guide member to be directed around obstacles and through curved vessels without causing damage to tissues or body structures as the tip of the guide member is advanced into or to the target area of the body. The guide member is advanced to the desired location within the body through a cannula. The cannula is then removed and a catheter is advanced over the guide member to the target area within the body.

Intravascular catheterization systems, such as those described above, have proven useful and efficient for both therapeutic and diagnostic purposes. For example, intravascular catheterization therapies, such as angioplasty and atherectomy, have been developed and widely used to treat vascular diseases or other conditions that occlude or reduce the lumen size of portions of a patients vascular system. In particular, balloon angioplasty has proven to be a useful and commonly-used treatment for obstructive coronary diseases. Additionally, intravascular catheterization systems have been used to perform various diagnostic procedures, such as angiographies, blood flow measurements, and ultrasonic imaging. These intravascular diagnostic systems may be used in conjunction with the aforementioned therapeutic intravascular catheterization systems or may be used in conjunction with other invasive techniques, such as coronary surgery.

Due to the small size or position of the target area and the tortuous passages through the patient's vasculature, positioning of a catheter or needle to such target areas can be a difficult and time consuming task requiring considerable skill on the part of the health-care provider. Although currently-available intravascular catheters that employ a separate guide member provide advantages relating to placement, these catheters obtain this advantage at the expense of size and stability. Accordingly, there is a need for needles and needle systems that possess very small profiles and that can be positioned in narrow, tortuous regions of a vasculature or in a target area having critical dimensions in the body of an animal or person.

SUMMARY OF THE INVENTION

The present invention relates to an improved needle for directional placement of the needle into or to a target area, such as a blood vessel or organ, for the purpose of performing an invasive procedure with a minimal amount of trauma to the target area. The needle comprises a connection hub, a needle shaft, and a flexible tip member connected to a distal end of the needle shaft to facilitate maneuvering the needle through tortuous passages within the body. The flexible tip member includes a blunt end that prevents or reduces trauma to tissues and vessels that are contacted with the distal portion of the needle during positioning of the needle.

The invention further comprises a flexible-tipped needle having a balloon sealingly attached to a distal end of the flexible tip member. The flexible-tipped balloon needle includes an inflatable balloon sealingly connected to the distal end of the flexible tip member. The inflatable balloon has an interior portion that is in fluid communication with a first bore located within the hub and a second bore located within the needle shaft. The flexible-tipped balloon is intended for use in a number of procedures requiring dilatation of target areas within the body, such as a ureter for the evacuation of stones or blood vessels for treating hardening or blockage of the vessels. Alternatively, or in addition to the balloon connected to the distal end of the flexible tip member, the flexible-tipped needle can include a balloon that surrounds and is scalingly connected to the needle shaft.

The invention also includes a flexible-tipped needle having an insulated needle shaft, an insulated flexible-tip member, a blunt conductive end and a conductive wire extending from the blunt conductive end to an apparatus for sending or receiving electromagnetic signals.

BRIEF DESCRIPTION OF THE SEVERAL VIEWS OF THE DRAWINGS

While the specification concludes with claims particularly pointing out and distinctly claiming that which is regarded as the present invention, the advantages of this invention can be more readily ascertained from the following description of the invention when read in conjunction with the accompanying drawings in which:

DETAILED DESCRIPTION OF THE INVENTION

Figure 1:
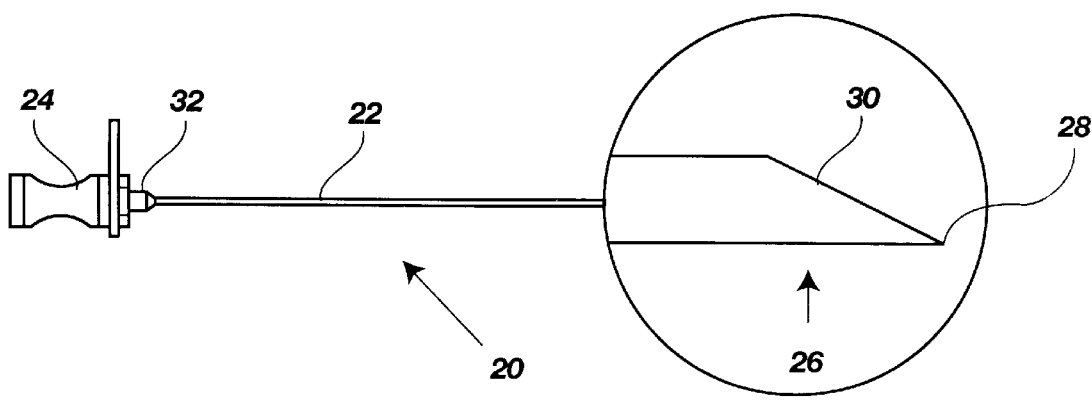
FIG. 1 is a side view of a prior art hypodermic needle, partly magnified to illustrate the configuration of a distal tip or end.

FIG. 1 illustrates a representative prior art hypodermic needle or cannula 20 including a needle shaft 22, a hub 24, and a needle tip 26. This prior art structure is shown in order to more fully describe the novelty of the present invention. The hub 24 is typically made of a plastic material and is shaped to lock to a syringe tip by friction or, alternatively, is shaped to interlock with a threaded syringe tip (as seen in Luer-Lock™ syringe systems). Attached to the hub 24 is the needle shaft 22, which is made of any suitable metal or alloy, such as stainless steel or hyperchrome steel. The hub 24 can additionally include a "bead" or stop 32 at an end opposite the end used for attachment of the hub 24 to the syringe.

The needle shaft 22 is attached to and in fluid communication with the hub 24 (or the bead 32) and is substantially rigid. Interior walls of the needle shaft 22 define a bore therethrough to allow passage of fluid through the needle shaft 22. Prior art needles are particularly characterized by their tips 26, which typically consist of long, tapering reinforced points 28 and beveled edges 30 of varying degrees. This particular configuration of the tips 26 varies according to the intended use. For example, long-bevel or long-taper needles are usually used for administering local anesthesia, aspirating, and subcutaneous administration. Short-bevel needles are usually used for intravenous administration and transfusions.

Figure 2:
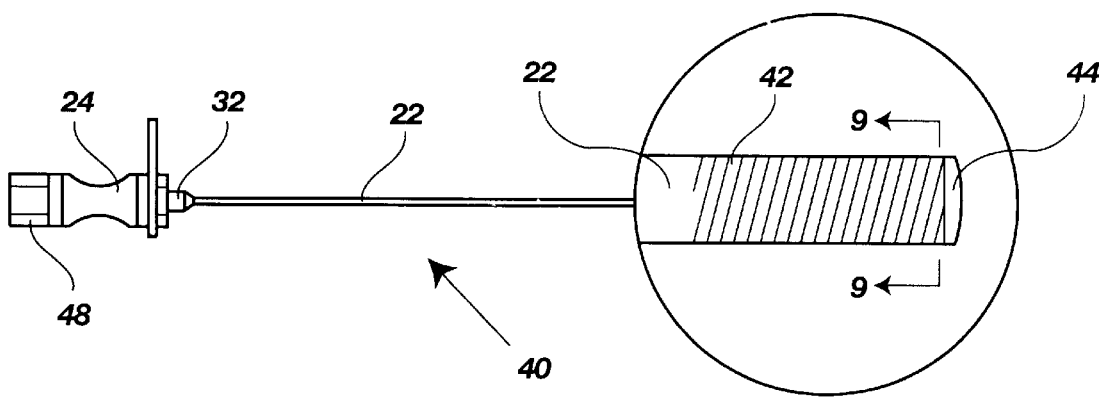
FIG. 2 is a side view of a spring tip needle made in accordance to the principles of the present invention and illustrates, in a partly-magnified view, the configuration of a flexible tip member attached to the shaft of the needle.

In contrast to the prior art hypodermic needle 20 shown in FIG. 1, FIG. 2 illustrates a spring-tip needle 40 configured in accordance with a first embodiment of the present invention. For purposes of simplicity, structures and elements shared in common between the prior art device and various embodiments of the present invention will be numbered identically. The spring-tip needle 40 includes the hub 24 that is in fluid communication with the needle shaft 22. Adjacent to the hub 24 is shown a stylet base 48, which is attached to a stylet 52 (FIG. 3) that, when inserted, is disposed within the hub 24, the needle shaft 22, and a spring tip 42 of the spring-tip needle 40. The spring-tip needle 40 can also include the bead 32, which is interposed between and in fluid communication with the needle shaft 22 and the hub 24. Unlike the prior art needle 20 of FIG. 1, the spring-tip needle 40 does not include the tip 26, or the reinforced points 28 and beveled edges 30 therein. Also, unlike most conventional needles having a round shaft, the needle shaft 22 of the spring-tip needle 40 can alternately be oval in shape.

In place of the tip 26, the spring-tip needle 40 includes the spring tip 42, which is attached to and in fluid communication with the needle shaft 22. The spring tip 42 serves to safely guide the spring-tip needle 40 through the tortuous passages of the vasculature or to a defined target area within the patient's body. The spring tip 42 can be attached to the needle shaft 22 by any suitable means (e.g., soldering, bonding, or molding). At a distal end of the spring tip 42 is a blunt end 44. Blunt end 44 is preferably an open-ended extension of the spring tip 42 which provides fluid communication with the hub 24, needle shaft 22, and spring tip 42. In such open-ended embodiments, blunt end 44 consists of a smooth-rimmed band or collar which allows for passage of the spring tip 42 in atraumatic fashion so that damage to tissue or vasculature does not occur. Alternatively, blunt end 44 can consist of a close-ended cap, which essentially blocks passage of fluids into or out of spring-tip needle 40. In such a "capped" embodiment, the spring tip 42 can be made to have a spread between the individual coils therein so as to permit passage of fluid through the soils of the spring tip 42.

As illustrated in FIG. 2, the external diameter or outer periphery of spring tip 42 is preferably equal to or less than the external diameter or outer periphery of the needle shaft 22. The diameters of the needle shaft 22 and the spring tip 42 are of any desirable gauge. For most applications the diameters typically range from 12-gauge (large diameter) to 27-gauge, although larger and smaller dimensions are commonly used for special procedures. The length of the spring-tip needle 40 and the needle shaft 22 can be of any desirable length depending on the specific procedure being performed, but is usually a length in the range between ¼ to 9 inches for most intravenous administration procedures.

Operation and use of the spring-tip needle 40 can best be described with reference to FIG. 3, which depicts a partially-magnified cross-sectional view of the spring-tip needle 40 of FIG. 2 and which further illustrates the guide wire or stylet 52 and a guiding cannula 56 that can be used in conjunction with the spring-tip needle 40. For example, when access to a blood vessel is desired, the stylet 52 is inserted into and through the hub 24, the needle shaft 22, and the spring tip 42. The stylet 52 can be made of any material, but preferably consists of a material that is "malleable," that is, which is bendable yet sufficiently rigid to maintain a desired shape when the spring-tip needle 40 is steered through a patient's vascular system. Alternatively, the stylet 52 can be made of a rigid material having either a straight or curved configuration. It is contemplated that the hub 24, needle shaft 22, and spring tip 42 have a sufficiently large diameter and size to accommodate the stylet 52.

In order to facilitate the introduction of the spring-tip needle 40 into an orifice or to aid in venipuncture, the guiding cannula 56 can be used. As shown in FIG. 3, the inner diameter of the guiding cannula 56 must be sufficiently large to accommodate the spring tip 42 and the needle shaft 22, and should be sufficiently flexible to permit passage of a spring-tip needle that has a bent configuration, while retaining the bend. The guiding cannula 56 can be any suitable catheter typically used for accessing vasculature or for accessing any other target area, such as tissue or an organ. The guiding cannula 56 includes a tip 58 and a beveled edge 60 to facilitate insertion of the guiding cannula 56 into tissue or vasculature. Insertion of the guiding cannula 56 into the patient is preferably performed with the spring-tip needle 40 already inserted therein. Alternatively, the site of entry into the patient can be independently accessed with the guiding cannula 56 prior to the insertion of the spring-tip needle 40 therein.

After the guiding cannula 56 has been positioned in the target area (e.g., patient's vessel), the spring-tip needle 40 is advanced to the target area. For example, where access to a particular area of a patient's vasculature is desired, the spring-tip needle 40 is advanced through the guiding cannula 56 and into the blood vessel. If it is desired to rotate the spring-tip needle 40, and in particular the spring tip 42, into a particular portion of the vessel (e.g., such as an angled portion of the vessel), the bent stylet 52 can be rotated by maneuvering the stylet hub 48 to cause rotation of the spring tip 42 (or a distal extremity thereof). To assist in positioning of the spring-tip needle 40 within the patient's body, a distal portion of the stylet 52 or the spring tip 42 can be marked with a radiopaque substance, so that movement of the marked section can be observed under a viewing device (e.g., a fluoroscope). Once the intended procedure has been performed, the spring-tip needle 40 and guiding cannula 56 can be withdrawn, leaving the spring-tip needle 40 in place.

Alternatively, the aforementioned procedure can be carried out by advancing the spring-tip needle 40 to a target area through the guiding cannula 56. Once the spring-tip needle 40 has reached a desired place, such as a blood vessel, the stylet 52 can be removed from within the spring-tip needle 40. Because the spring tip 42 is no longer held in a particular configuration by the stylet 52, the spring-tip needle 40 can be freely advanced through the vessel. Due to the combination of the blunt end 44 and the spring tip 42, which together follow the contours of the pathways (i.e., vessels or cavities) of the body through which they travel, the spring-tip needle can be safely advanced through a curved vessel or target area without the typically-experienced tissue trauma.

Figure 4:
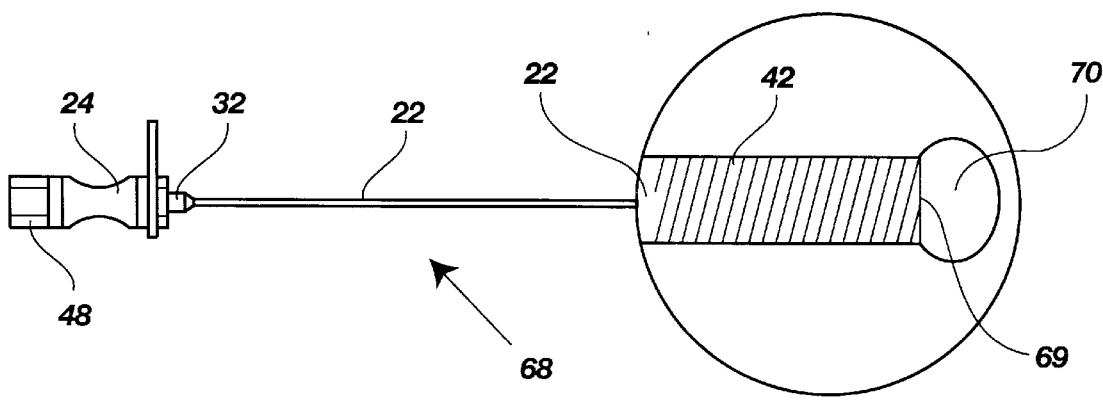
FIG. 4 is a side view of a second embodiment of the spring tip needle of the present invention which includes an inflatable balloon at a distal end of the flexible tip member.

FIG. 4 illustrates another embodiment of the spring-tip needle of the present invention. The spring-tip needle 68 of FIG. 4 is similar to the spring-tip needle 40 described thus far, except that spring-tip needle 68 further includes an inflatable balloon 70 attached to the distal end of the spring tip 42. The balloon 70 (shown inflated) extends distally from the distal end 69 of the spring tip 42. In its deflated state, the balloon 70 is substantially contained within the spring tip 42. The balloon can be made of any suitable material, such as a polyolefin, which is expandable, non-toxic, and flexible.

The balloon 70 is in fluid communication with the hub 24 and needle shaft 22 of the spring-tip needle 68. Preferably, the balloon 70 is sealably connected to the distal end 69 of spring tip 42 by any suitable adhesive and sealing material, such as a cyanoacrylate or epoxy material. Such a configuration facilitates the use of the stylet 52, if such use is desired, by allowing the stylet 52 and the balloon 70 to simultaneously extend through the needle shaft 22 and the spring tip 42. Alternatively, the balloon 70 can be connected to an internal portion of the needle shaft 22 and positioned to extend through the inside of the spring tip 42.

The balloon length will vary depending upon the size of the spring-tip needle 68, which needle can have a length up to about two feet for most applications. Therefore, the length of the balloon 70 should be sufficient to permit fluid communication throughout the spring-tip needle 68 and extension beyond the distal end of the spring tip 42 following inflation of the balloon 70. The balloon can be made and shaped to permit expansion of an exposed portion (that portion of the balloon 70 shown in FIG. 4) to any desirable diameter, which will naturally depend on the dimension of the area being dilated with the balloon.

Figure 3:
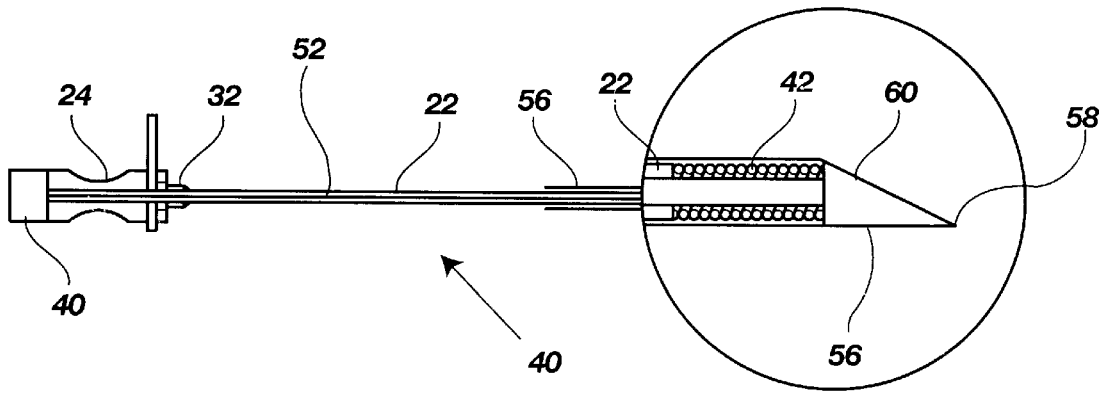
FIG. 3 is a cross-sectional view of the spring tip needle of the present invention, further illustrating the relative position of the spring tip needle in relation to a stylet and a guiding catheter which can be used in conjunction with the spring tip needle.

In use, the spring-tip needle 68 is positioned at a desired location by following the technique described in conjunction with FIG. 3. Once the spring tip 42 is positioned at a desired location, the balloon is inflated by activating an inflation/deflation device (not shown). The inflation/deflation device is used to inflate or deflate the balloon 70 at the distal end of the spring-tip needle 68. The inflation/deflation device is sealably connected to the hub 24 or, alternatively, is connected to a mating member which is, in turn, connected to the hub 24. Inflation of the balloon 70 causes radially directed stretching forces to be applied to the areas surrounding the balloon 70. This technique can be applied to a number of procedures, such as, dilatation of a ureter for the evacuation of stones, dilatation of blood vessels for treating hardening or blockage of a vessel (e.g., angioplasty procedures), and dilatation of nerve areas to create a lesion in specific nerves. Use of the spring-tip needle 68 is only limited by the inventiveness of the health care practitioner.

Due to the small dimensions of the spring-tip needle 68, more than one spring-tip needle 68 can be advanced and positioned to carry out the aforementioned procedures. For example, once the first spring-tip needle 68 has been placed in the appropriate position and the tissue plane has been established, a second spring-tip needle 68 can be passed to the same or an adjacent location. Additionally, where advantageous, dilatation of a target area can be accomplished by introducing a plurality of spring-tip needles 68 through multiple sites, such as by accessing a number of different merging blood vessels.

Figure 5:
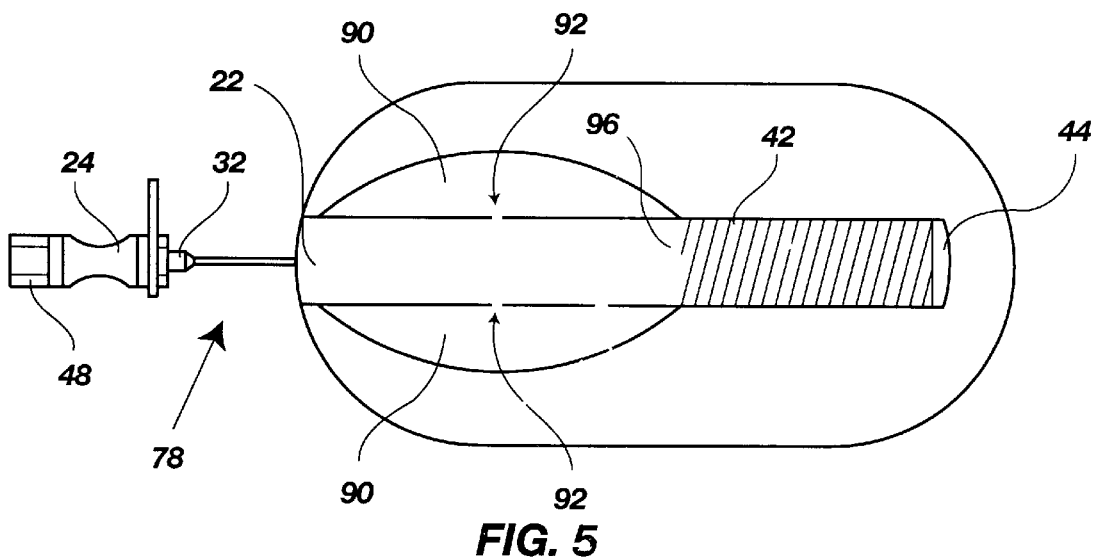
FIG. 5 is a side view of a third embodiment of the spring tip needle of the present invention which includes an inflatable balloon disposed between the hub of the needle and the flexible tip member of the needle.

FIG. 5 illustrates an alternative embodiment of a spring-tip needle having an attached balloon. The spring-tip needle 78 of FIG. 5 is functionally similar to the spring tip needle 68 described in conjunction with FIG. 4, except that spring-tip needle 78 includes a balloon 90 that surrounds the needle shaft 22, as opposed to having a balloon that is attached to the distal end of the spring tip 42. The spring-tip needle 78 includes a blunt end 44 that consists of a close-ended cap, which essentially blocks passage of fluids into or out of spring-tip needle 78. Specifically, a proximal end of the balloon 90 (shown inflated) is secured to the spring-tip needle 78 anywhere along the needle shaft 22, preferably at a point distal to the hub 32. A distal end of the balloon 90 is secured to a distal end 96 of the needle shaft 22, preferably at a position adjacent the spring tip 42, such as the junction 96.

The interior of the balloon 90 is in fluid communication with the needle shaft 22 of the spring-tip needle 78 via one or more apertures 92 on the needle shaft 22. The balloon ends are attached or secured to the needle shaft 22 by any suitable adhesive and sealing material, such as epoxy. The balloon length will vary depending upon the size of the spring-tip needle 68 and the desired area of balloon contact.

Figure 6:
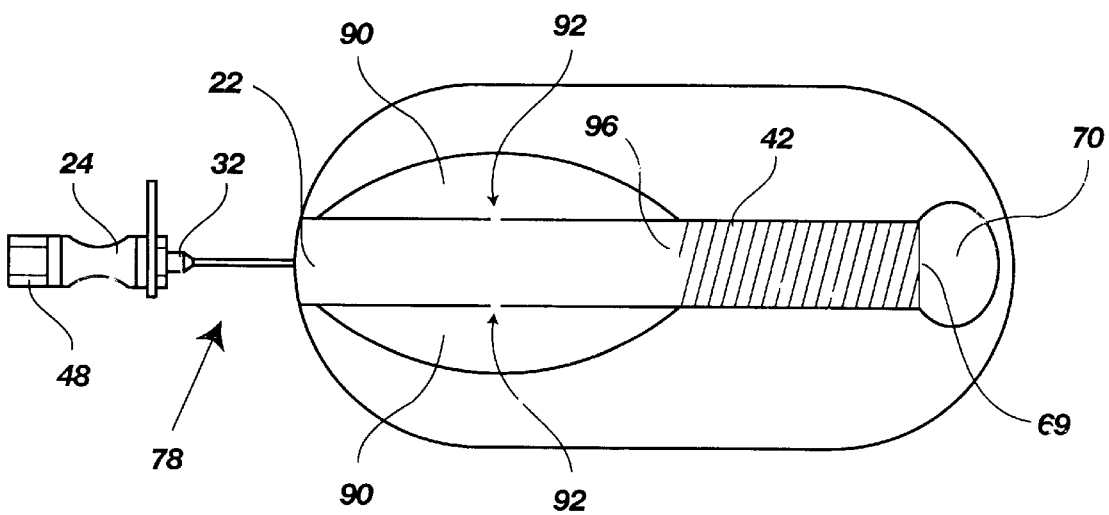
FIG. 6 is a side view of a fourth embodiment of the spring tip needle of the present invention which includes an inflatable balloon disposed between the hub of the needle and the flexible tip member of the needle and another inflatable balloon at a distal end of the flexible tip member.

The balloon can be made and shaped to permit expansion of an exposed portion thereof to any desirable diameter and to a length covering up to the entire length of the needle shaft 22. In use, positioning and inflation of spring-tip needle 78 can be accomplished by following the technique described in conjunction with FIG. 4. Alternatively, the embodiments of FIGS. 4 and 5 can be combined to include two balloons, one surrounding the needle shaft 22 and the other attached to the distal end of the spring tip 42 (wherein blunt end 44 consists of an open-ended extension of the spring tip 42), as illustrated in FIG. 6.

Figure 7:
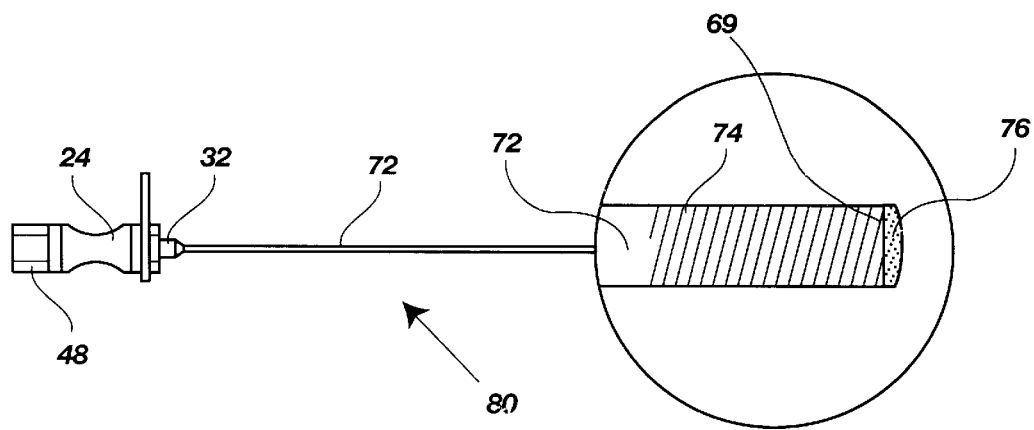
FIG. 7 is a side view of a fifth embodiment of the spring tip needle of the present invention which includes a conductive tip for sending or receiving electromagnetic signals.

In FIG. 7 is shown yet another embodiment of the present invention used to provide electrical or radiofrequency stimulation to a target area. This alternate embodiment of the spring-tip needle 80 is structurally similar to the spring-tip needle 40 of FIG. 2, except that the needle shaft 72 and the spring tip 74 are insulated to the distal end of the spring tip 74. The needle shaft and the spring tip 74 can be made of insulative materials or, alternatively, can be covered with a layer of insulative materials. Suitable insulative materials include any material known in the art having sufficient mechanical strength and good electrical and thermal insulating properties.

Conductive tip 76 is identical in shape and form to the blunt end 44 of FIG. 2 and is made of any material having good conductive characteristics, such as gold, copper, steel, and alloys thereof. The size of the conductive tip 76 varies according to use and the desired area of contact, most preferably ranging in size from about 2 mm to about 15 mm in length and from about 25 gauge to about 12 gauge in diameter. The conductive tip 76 is connected to an external energy source (e.g., an electromagnetic generator, such as an electrical, laser, or radiofrequency generator), which transfers energy from the generator through a conductive wire or, alternatively, through internal portions of the needle shaft 72 and spring tip 74 having insulated exteriors, and to the conductive tip 76. Alternatively, where a larger area of contact is desired, only a portion of spring tip 74 can be made or covered with a layer of insulative materials so as to expand the area of conductivity beyond the conductive tip 76.

In operation, the spring-tip needle 80 is positioned at a desired location by following the technique described in conjunction with FIG. 3. Once the conductive tip 76 is positioned at or near a target site, the energy generator is activated to supply power via wires to the conductive tip 76. In this fashion, target site tissue (e.g., heart tissue) is exposed to electrical or radiofrequency power to correct a particular problem (e.g., tachycardia or arrhythmia). The conductive tip 76 may alternatively or additionally include electrodes that are connected to external monitoring equipment, such as EKG machines or other monitoring and mapping equipment, to receive signals and data from the target area for various purposes, such as diagnosing electrical cardiac impulses.

Figure 8:
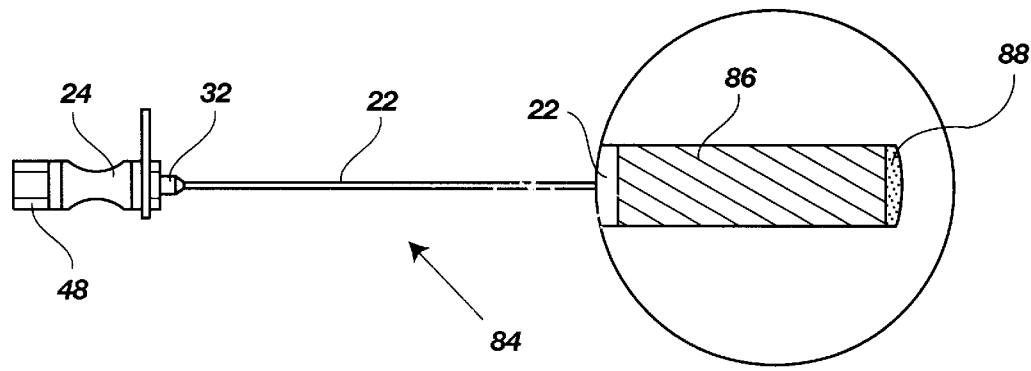
FIG. 8 is a side view of a sixth embodiment of the spring tip needle of the present invention which includes a flexible tip.

FIG. 8 illustrates a modified embodiment of the spring-tip needle of FIG. 2, wherein a flexible tip 86 replaces the spring tip 42. Like the spring tip 42 of FIG. 2, the flexible tip 86 of the instant flexible tip needle 84 includes an open-ended blunt end 88 at the terminal end thereof. The flexible tip 86 provides the same functional advantages of the spring tip 42, but is made of a thermoplastic material, such as polyethylene, having the same flexibility and high strength characteristics. The flexible tip 86 is sealably connected to the distal end of the needle shaft 22 by any suitable means, such as by way of heat bonding or application of an adhesive material (e.g., a cyanoacrylate or epoxy material) therebetween. As previously described with reference to the spring tip 42 of FIG. 2, the flexible tip 86 can be configured and shaped in various desirable lengths, widths, and diameters.

Figure 9:
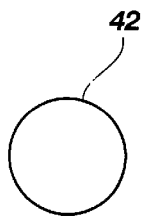
FIG. 9 is a cross-sectional view of a seventh embodiment of the spring tip needle taken along lines 9—9 of FIG. 2 which includes an round shaped spring tip and needle shaft.
Figure 10:
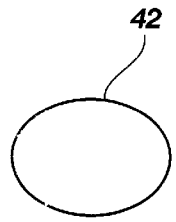
FIG. 10 is a cross-sectional view of an eighth embodiment of the spring tip needle which includes an oval shaped spring tip and needle shaft.
Figure 12:
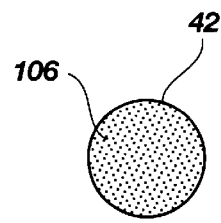
FIG. 12 is an end view of a tenth embodiment of the flexible tip member of the spring tip needle which includes a sealing barrier at the distal end of the flexible tip member.
Figure 11:
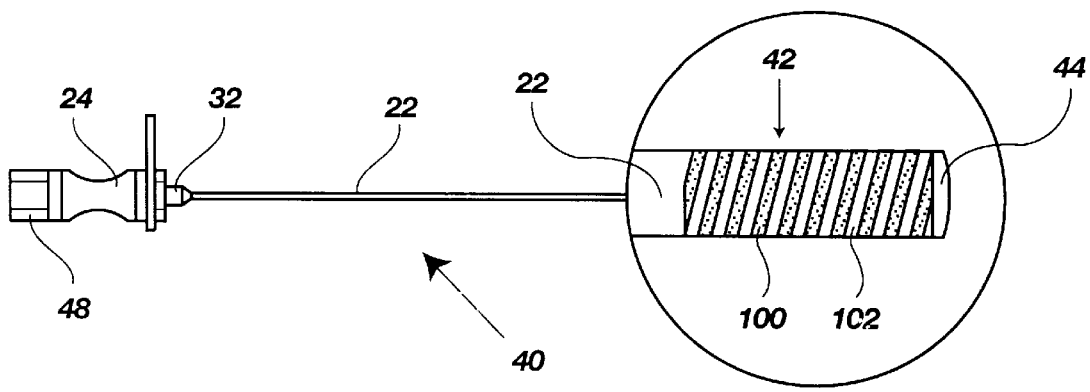
FIG. 11 is a side view of a ninth embodiment of the spring tip needle of the present invention which includes a flexible tip member having spaced apart coils.
Figure 13:
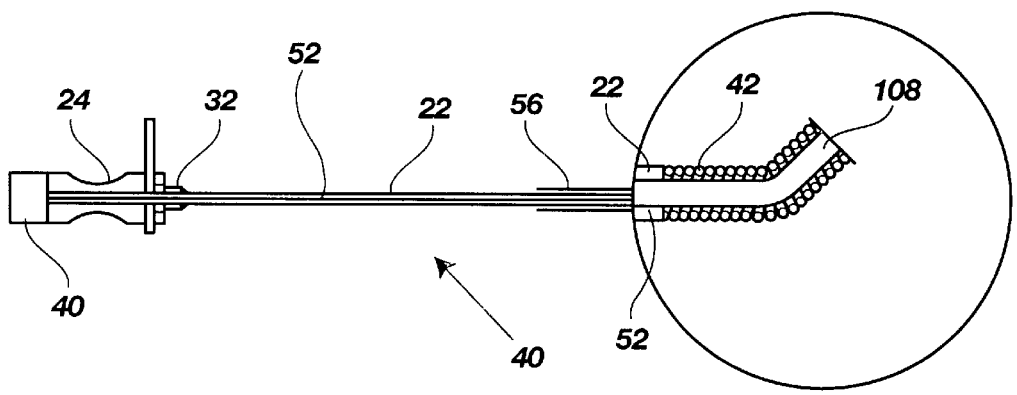
FIG. 13 is a cross-sectional view of an eleventh embodiment of the spring tip needle of the present invention which includes a stylet that is curved at a distal end thereof.

While the invention has been described with reference to specific embodiments, the description is illustrative of the invention and is not to be construed as limiting the invention. Various modifications and applications may occur to those skilled in the art without departing from the true spirit and scope of the invention as defined by the appended claims. For example, the spring tip needle 40 of the present invention can be configured to have a round or oval cross section, as shown in FIGS. 9 and 10, respectively. Alternatively, the spring tip 42 of the spring tip needle 40 can be formed in such a manner that the adjacent coils 100 thereof are spaced apart so as to permit fluid flow through gaps 100 formed between coils 100, as shown in FIG. 11. Where fluid flow through the distal end of the spring tip 42 is undesirable, the spring tip 42 can include a sealing barrier 106 thereon, as shown in FIG. 12. A final exemplary modification can also include a curved stylet 108, which is illustrated in FIG. 13, to facilitate placement of the spring tip needle 40 within a patient's vasculature.

What is claimed is:

1. A flexible-tipped needle comprising:
   a connection hub having a proximal end and a distal end, said proximal end being shaped to receive a syringe tip, said hub being shaped to define a first bore therethrough;
   a substantially rigid insulated needle shaft having a distal end and a proximal end extending from and in fluid communication with said distal end of said connection hub, said needle shaft being shaped to define a second bore therethrough, said first bore being in fluid communication with said second bore; and
   an insulated flexible tip member having a distal end and a proximal end, said proximal end being sealingly connected to and in fluid communication with said distal end of said needle shaft, said distal end of said flexible tip member having a blunt conductive end, said flexible member being shaped to define a third bore therethrough, said second bore being in fluid communication with said third bore; and
   a guiding cunnula having a catheter tip and a beveled edge to form a sharp edge, said guiding cannula receiving said needle through and having an internal diameter larger than the external diameter of said flexible tip member.

2. A flexible-tipped needle comprising:
   a connection hub having a first end and a second end, said first end being shaped to receive a syringe tip, said hub being shaped to define a first bore therethrough;
   an insulated needle shaft having a first end and a second end extending from said first end of said connection hub, said needle shaft being shaped to define a second bore therethrough, said first bore being in fluid communication with said second bore;

a coil spring having a first end and a second end, said first end being sealingly connected to and in fluid communication with said second end of said needle shaft, said second end of said flexible tip member having a blunt conductive end, said flexible member being shaped to define a third bore therethrough, said second bore being in fluid communication with said third bore, wherein said coil spring further comprises having an electrically insulative material on at least a portion of exposed surfaces thereof; and a conductive wire extending from said blunt conductive end to an apparatus for sending or receiving electromagnetic signals.

3. The needle of claim 2, wherein a diameter of said third bore is no larger than a diameter of said second bore.

4. A flexible-tipped needle comprising:

a connection hub having a first end and a second end, said first end being shaped to receive a syringe tip, said hub being shaped to define a first bore therethrough;

an insulated needle shaft having a first end and a second end extending from said first end of said connection hub, said needle shaft being shaped to define a second bore therethrough, said first bore being in fluid communication with said second bore;

a coil spring having a first end and a second end, said first end being sealingly connected to and in fluid communication with said second end of said needle shaft, said second end of said flexible tip member having a blunt conductive end, said flexible member being shaped to define a third bore therethrough, said second bore being in fluid communication with said third bore;

a conductive wire extending from said blunt conductive end to an apparatus for sending or receiving electromagnetic signals; and a guiding cannula having a catheter tip and a beveled edge to form a sharp edge, said guiding cannula having an internal diameter larger than the external diameter of said flexible tip member.

* * * * *

UNITED STATES PATENT AND TRADEMARK OFFICE
CERTIFICATE OF CORRECTION

PATENT NO. : 6,371,943 B1
APPLICATION NO. : 09/353159
DATED : April 16, 2002
INVENTOR(S) : Gabor J. Racz and Bruce B. Whitcavitch It is certified that error appears in the above-identified patent and that said Letters Patent is hereby corrected as shown below:

In the drawings:

| | | |
|---|---|---|
| FIGURE 3, | | change the left-most occurrence of "40" to --48-- |
| FIGURE 13, | | change the left-most occurrence of "40" to --48-- |

In the specification:

| | | |
|---|---|---|
| COLUMN 3, | LINE 36, | change "an round" to --a round-- |
| COLUMN 5, | LINE 40, | change "hub 48" to --base 48-- |
| COLUMN 8, | LINE 22, | change "spring tip needle" to --spring-tip needle-- |
| COLUMN 8, | LINE 25, | change "spring tip needle" to --spring-tip needle-- |
| COLUMN 8, | LINE 26, | change "coils 100" to --coils 102-- |
| COLUMN 8, | LINE 28, | change "coils 100," to --coils 102,-- |
| COLUMN 8, | LINE 33, | change "spring tip" to --spring-tip-- |

In the claims:

| | | | |
|---|---|---|---|
| CLAIM 1, | COLUMN 8, | LINE 56, | change "cunnula" to --cannula-- |
| CLAIM 1, | COLUMN 8, | LINE 59, | change "then the external" to --than an external-- |
| CLAIM 2, | COLUMN 9, | LINE 6, | change "flexible tip member" to --coil spring-- |
| CLAIM 2, | COLUMN 9, | LINE 7, | change "flexible member" to --coil spring-- |
| CLAIM 4, | COLUMN 10, | LINE 9, | change "flexible tip member" to --coil spring-- |
| CLAIM 4, | COLUMN 10, | LINE 10, | change "flexible member" to --coil spring-- |
| CLAIM 4, | COLUMN 10, | LINE 18, | change "than the external" to --than an external-- |
| CLAIM 4, | COLUMN 10, | LINE 19, | change "flexible tip member." to --coil spring.-- |

UNITED STATES PATENT AND TRADEMARK OFFICE
CERTIFICATE OF CORRECTION

PATENT NO. : 6,371,943 B1  Page 2 of 3
APPLICATION NO. : 09/353159
DATED : April 16, 2002
INVENTOR(S) : Gabor J. Racz and Bruce B. Whitcavitch It is certified that error appears in the above-identified patent and that said Letters Patent is hereby corrected as shown below:

Please replace FIG. 3 with the following:

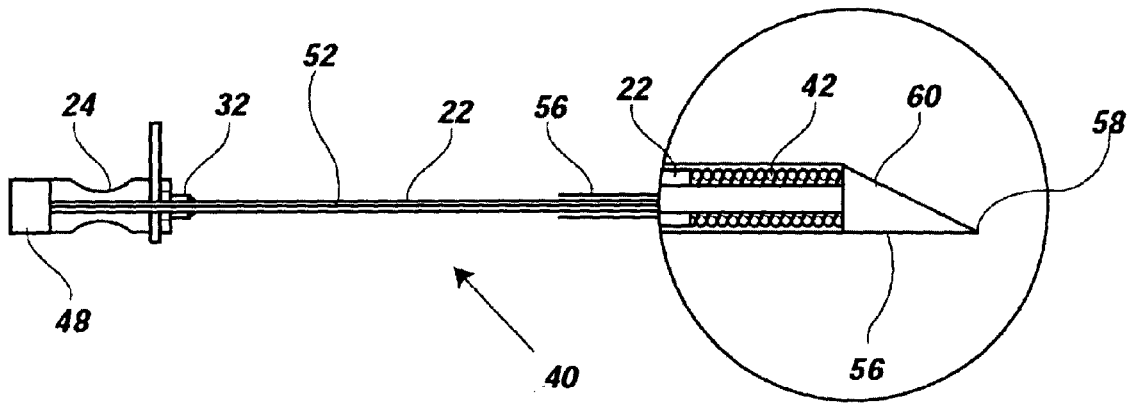

FIG. 3

UNITED STATES PATENT AND TRADEMARK OFFICE
CERTIFICATE OF CORRECTION

PATENT NO.        : 6,371,943 B1                                    Page 3 of 3
APPLICATION NO.   : 09/353159
DATED             : April 16, 2002
INVENTOR(S)       : Gabor J. Racz and Bruce B. Whitcavitch It is certified that error appears in the above-identified patent and that said Letters Patent is hereby corrected as shown below:

Please replace FIG. 13 with the following:

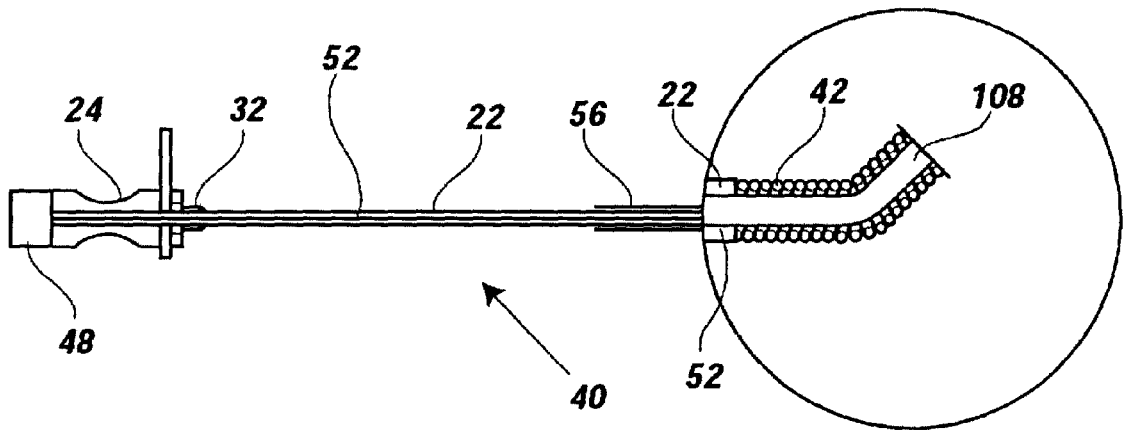

FIG. 13

Signed and Sealed this

Seventeenth Day of October, 2006

JON W. DUDAS
*Director of the United States Patent and Trademark Office*